United States Patent
Ropars et al.

(10) Patent No.: US 9,758,798 B2
(45) Date of Patent: Sep. 12, 2017

(54) PROCESS FOR THE PRODUCTION OF ETHANOL AND SOLVENTS FROM LIGNOCELLULOSIC BIOMASS WITH RECYCLING OF AN ETHANOLIC LIQUOR OBTAINED FROM THE FERMENTATION OF PENTOSES

(75) Inventors: Marcel Ropars, Palaiseau (FR); Caroline Aymard, Lyons (FR); Rejane Dastillung, Lyons (FR); Sandra Menir, Gonesse (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 139 days.

(21) Appl. No.: 14/111,869

(22) PCT Filed: Mar. 27, 2012

(86) PCT No.: PCT/FR2012/000108
§ 371 (c)(1),
(2), (4) Date: Jan. 23, 2014

(87) PCT Pub. No.: WO2012/140332
PCT Pub. Date: Oct. 18, 2012

(65) Prior Publication Data
US 2014/0134692 A1 May 15, 2014

(30) Foreign Application Priority Data
Apr. 14, 2011 (FR) ..................... 11 01147

(51) Int. Cl.
C12P 7/14 (2006.01)
C12P 7/10 (2006.01)

(52) U.S. Cl.
CPC ........ *C12P 7/14* (2013.01); *C12P 7/10* (2013.01); *Y02E 50/16* (2013.01)

(58) Field of Classification Search
None
See application file for complete search history.

(56) References Cited

U.S. PATENT DOCUMENTS

| 8,123,864 B2 | 2/2012 | Christensen et al. |
| 8,460,473 B2 | 6/2013 | Christensen et al. |
| 2009/0093027 A1 | 4/2009 | Balan et al. |
| 2010/0041119 A1 | 2/2010 | Christensen et al. |
| 2010/0159552 A1 | 6/2010 | Benson et al. |
| 2010/0221803 A1* | 9/2010 | Shimoda et al. ............ 435/161 |
| 2012/0100585 A1 | 4/2012 | Ropars et al. |
| 2012/0138246 A1 | 6/2012 | Christensen et al. |
| 2013/0143263 A1 | 6/2013 | Christensen et al. |

FOREIGN PATENT DOCUMENTS

| WO | WO-2007 009463 | 1/2007 |
| WO | WO-2010 130888 | 11/2010 |

OTHER PUBLICATIONS

Tu M et al. Recycling cellulases during the hydrolysis of steam exploded and ethanol pretreated lodgepole pine. 2007. Biotechnology Progress. 23, 1130-1137.*
Gi-Wook C et al. Isolation and characteriziation of ethanol-producing Schizosaccharomyces pombe CHFY0201. 2010. 20(4), 828-834.*
Dutta, A. et al., "An economic comparison of different fermentation configurations to convert corn stover to ethanol using z. mobilis and *Saccharomyces*," American Institute of Chemical Engineers Biotechnol. Prog., 2010, vol. 26, pp. 64-72.
Hamelinck, C. N. et al., "Ethanol from lignocellulosic biomass : techno-economic performance in short-, middle- and long-term," Biomass and Bioenergy, 2005, vol. 28, No. 384-410.
International Search Report for PCT/FR2012/000108, Date of the actual completion of the international search: Aug. 17, 2012, Date of mailing of the international search report: Aug. 28, 2012.

\* cited by examiner

*Primary Examiner* — Paul Holland
(74) *Attorney, Agent, or Firm* — Millen, White, Zelano and Branigan, P.C.

(57) ABSTRACT

Embodiments provided here relate to second generation processes for the production of alcohols or solvents, wherein the lignocellulosic or cellulosic biomass undergoes a pre-treatment before being converted into ethanol after an enzymatic hydrolysis and fermentation. The glucidic polymers of the pre-treated plant material are hydrolysed by cellulases. The alcoholigenic microorganisms used for the ethanolic fermentation principally use hexoses, for example, glucose and mannose. The alcohols of the liquor, with or without separation of the suspended material are extracted by distillation. The stillage, containing pentoses which have not been used, are fermented into an ex-pentose ethanolic liquor and at least a portion of the liquor is recycled upstream of the enzymatic hydrolysis. The enzymatic hydrolysis and the ethanolic fermentation are thus carried out separately or simultaneously in the presence of a portion of the ethanolic liquor, which mixture does not interfere with the performance of the enzymes and microorganisms.

12 Claims, 2 Drawing Sheets

PROCESS FOR THE PRODUCTION OF ETHANOL AND SOLVENTS FROM LIGNOCELLULOSIC BIOMASS WITH RECYCLING OF AN ETHANOLIC LIQUOR OBTAINED FROM THE FERMENTATION OF PENTOSES

FIELD OF THE INVENTION

The context of the present invention is in so-called "second generation" processes for the production of alcohols and/or solvents from lignocellulosic biomass. More particularly, it concerns a process for the production of ethanol and/or solvents.

PRIOR ART

Lignocellulosic biomass represents one of the most abundant renewable sources on the planet. The substrates under consideration are highly varied, since they concern both ligneous substrates (deciduous and coniferous), agricultural by-products (straw) or those from industries generating lignocellulosic waste (agroalimentary or paper industries).

Lignocellulosic biomass is composed of three principal polymers: cellulose (35% to 50%), hemicellulose (20% to 30%), which is a polysaccharide essentially constituted by pentoses and hexoses, and lignin (15% to 25%), which is a polymer with a complex structure and a high molecular weight composed of aromatic alcohols linked via ether bonds.

Those various molecules are responsible for the intrinsic properties of the plant wall and are organized into a complex network.

Cellulose and possibly hemicelluloses are the targets for enzymatic hydrolysis, but they cannot be directly accessed by the enzymes. For this reason, such substrates have to undergo a pre-treatment preceding the enzymatic hydrolysis step. The pre-treatment is intended to modify the physical and physico-chemical properties of the lignocellulosic material with a view to improving the accessibility to the cellulose trapped in the matrix of lignin and hemicellulose.

Many techniques exist for carrying out such a pre-treatment: acid digestion, alkaline digestion, steam explosion, organosolv processes, etc. The efficiency of the pre-treatment is measured both by the material balance at the end of the pre-treatment (recovery yield for sugars in the form of soluble monomers or oligomers, or insoluble polymers) and also by the susceptibility of the cellulosic and hemicellulosic residues to hydrolysis.

Processes for the production of alcohols and/or solvents from lignocellulosic biomass, known as "second generation processes", comprise at least the following steps:
substrate pre-treatment;
enzymatic hydrolysis of the pre-treated substrate;
fermentation of the hydrolysate obtained; and
separation/purification of the alcohol and/or solvent obtained after fermentation.

The economic validity of that type of process for the production of alcohol and/or solvent is difficult to achieve even for operators with large mobilisable resources at their disposal. A plurality of stations have a major impact on the overall cost including the plant material resource and the energy for extraction, usually carried out by distillation. Optimizing that type of process necessarily includes optimizing upgrading of all of the sugars, in particular the pentoses obtained from hydrolysis by the most suitable microorganisms.

Wild type alcoholigenic yeasts such as *Saccharomyces cerevisiae* are known to be the most effective microorganisms for the conversion of hexoses into ethanol. The yields for the conversion of hexoses into ethanol are generally in the range 0.46 to 0.48 by weight, but are only 0.35 to 0.40 for the conversion of pentoses into ethanol. Wild type yeasts of this type are not capable of converting pentoses without genetic modification. Using genetically modified microorganisms complicates management of the facilities and that of the process. Thus, modified yeasts will always primarily use hexoses and they can only then use those pentoses in the presence of a limited quantity of glucose which has to be supplied to the microorganism continuously. The rate of consumption of pentoses is known to be much lower than that of hexoses (Olsson and Hahn-Hagerdahl, 1996; Hahn-Hägerdal et al., 2007).

Upgrading pentoses into ethanol has always been a major problem for the process as a whole. While certain wild type yeasts are capable of converting such pentoses into ethanol, they have to be cultivated under micro-aerobiotic conditions in order to produce satisfactory performances. Further, the medium is preferably essentially constituted by pentoses, because the performance of those yeasts is much poorer than that of *Saccharomyces cerevisiae* for upgrading hexoses (Olsson and Hahn-Hagerdahl, Enzymes Microb. Techno vol 18, 1996; Hahn-Hägerdal et al., Appl. Microbiol. Biotech 74, 937-953, 2007).

Other solutions may be envisaged when using genetically modified yeasts which are capable of using xylose properly, after having consumed the glucose or consuming it concomitantly. However, such yeast types generally require limited and controlled injection of glucose in order to ensure xylose consumption, which substantially complicates control of the process. Further, such genetically modified organisms have to be cultivated under strict confinement conditions, which are not very compatible with mass production in very large, rural facilities.

In addition, the extraction of alcohols carried out by distillation is a particularly energy-consuming activity. It can be seen that, in order to improve the economic balance of ethanol production, the volumes of water which have to be heated should be reduced, in particular by means of recycling or combining various streams which concentrate the solvents.

The present invention describes a process for the production of alcohols and/or solvents in which a portion of the ethanolic liquor produced principally from the pentoses alone is recycled to the line for the conversion of hexoses into ethanol in order to reduce the overall cost of extraction.

SUMMARY OF THE INVENTION

The present invention pertains to a process for the production of alcohols and/or solvents known as a second generation process, in which the lignocellulosic or cellulosic biomass undergoes a pre-treatment before being converted into ethanol after an enzymatic hydrolysis and an ethanolic fermentation. The glucidic polymers of the pre-treated plant material are hydrolysed by cellulases. The alcoholigenic microorganisms used for the ethanolic fermentation principally use hexoses, preferably glucose and mannose. The alcohols of the liquor, with or without separation of the suspended material (SM), are extracted by distillation. The stillage principally contains pentoses which have not been used. These pentoses are fermented into an ex-pentose ethanolic liquor and at least a portion of this liquor obtained thereby is recycled upstream of the enzymatic hydrolysis.

The enzymatic hydrolysis and the ethanolic fermentation are thus carried out separately or simultaneously in the presence of a portion of the ethanolic liquor, which mixture does not interfere with the performance of the enzymes and microorganisms under the operating conditions.

DETAILED DESCRIPTION OF THE INVENTION

Figure 1:
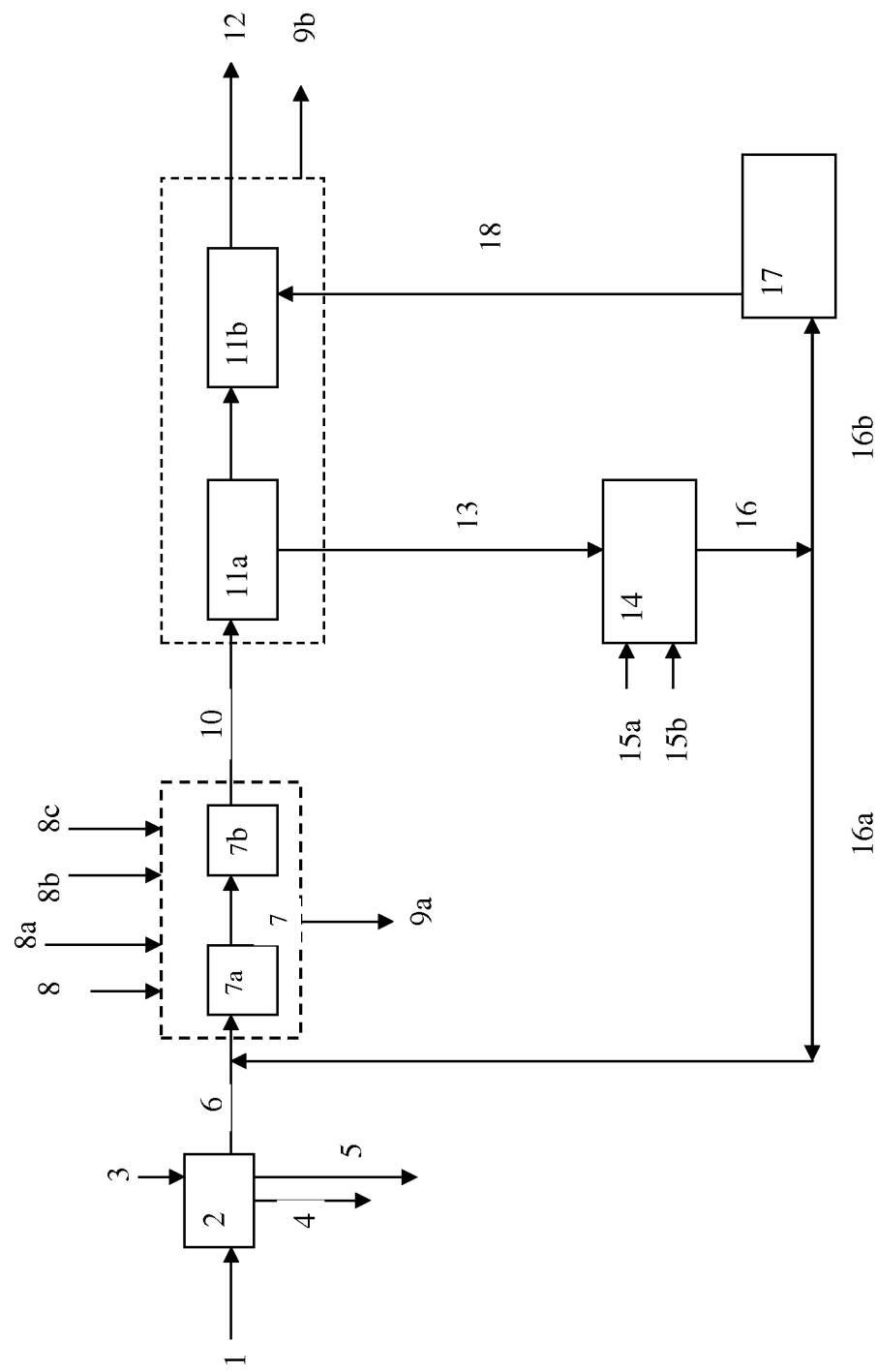
FIG. 1 is a diagrammatic representation of a process for the production of alcohols and/or solvents from lignocellulosic substrates, comprising a step for recycling ex-pentose ethanolic liquor in accordance with a first embodiment.

The present invention describes a process for the production of alcohols and/or solvents from cellulosic or lignocellulosic biomass, comprising at least the following steps:
 a) a step for thermochemical pre-treatment of a cellulosic or lignocellulosic substrate;
 b) an optional step for washing the pre-treated substrate and for adjusting the pH;
 c) a step for enzymatic hydrolysis of the pre-treated substrate, optionally washed, using cellulolytic and/or hemicellulolytic enzymes producing a hydrolysate and a water-insoluble residue;
 d) a step for ethanolic fermentation of the hexoses contained in the hydrolysate obtained from step c) into ethanol by an alcoholigenic microorganism and for obtaining an ex-hexose ethanolic liquor;
 e) an extraction step comprising:
  e1) separating and purifying the ethanol and/or the solvents obtained from step d); and
  e2) separating a solid cake containing the insoluble residue and obtaining stillage;
 f) a step for ethanolic fermentation of the pentoses contained in at least one of the streams obtained from one of the preceding steps with a pentose-fermenting microorganism and for obtaining an ex-pentose ethanolic liquor;
 in which at least a portion of the ex-pentose ethanolic liquor obtained in step f) is recycled upstream of at least one of the enzymatic hydrolysis c) and/or ethanolic fermentation d) steps.

In the context of the present invention, the term "pentoses" denotes soluble monomers and oligomers of sugars containing 5 carbon atoms and the term "hexoses" means soluble monomers and oligomers of sugars containing 6 carbon atoms.

The abbreviation DM is given to the dry matter (solids and solubles) present in a medium and the abbreviation SM is given to material in suspension (solids) present in a medium.

The term "ex-hexose ethanolic liquor" denotes the liquor obtained from fermentation by hexose-fermenting microorganisms.

The term "ex-pentose ethanolic liquor" denotes the liquor obtained from fermentation by pentose-fermenting microorganisms.

By means of the process of the present invention, it is possible to substantially improve the energy balance of the extraction step. In fact, the ethanolic liquor obtained respectively from the fermentation of hexoses and pentoses are combined, and so a single extraction step is necessary. The saving is approximately 5% to 50%.

Advantageously, this extraction step is carried out on a liquor with a higher alcoholic content, hexose conversion being operated in the medium containing ethanol obtained from the fermentation of pentoses.

The process of the invention preferably uses different microorganisms in steps d) and f), the first being adapted to the fermentation of hexoses, the others being capable of fermenting only pentoses, preferably without a continuous and limiting supply of glucose.

The cellulosic or lignocellulosic substrate used in the process of the present invention is selected from the most varied of biomasses, but more particularly from coniferous arborescent species (softwood such as spruce or pine) or deciduous species (hardwood such as eucalyptus) or from agricultural lignocellulosic waste (wheat straw, rice straw, etc.) or from dedicated cultures (miscanthus, switchgrass).

Prior to the thermochemical pre-treatment, the biomass may undergo a mechanical treatment, for example a type of grinding.

The term "thermochemical pre-treatment" is understood to mean any pre-treatment known to the skilled person employing chemical agents, which may be alkaline or acidic, and/or heating the biomass.

The pre-treatment carried out in step a) may be carried out using many configurations known to the skilled person (Hendriks and Zeeman, Bioresource Technology, 100(2009) 10-18; Ogier et al, Oil & Gas Science and Technology, vol 54 (1999) p 67-94). Alkaline pre-treatment by digestion in the presence of caustic soda, a pre-treatment by ammonia fibre explosion (AFEX) or a percolation pre-treatment using ammonia with a recycle, known as ARP (Ammonia Recycle Percolation) may be cited. It is also possible to cite acid digestion or steam explosion under acidic conditions.

Preferably, the pre-treatment of step a) is acid digestion or steam explosion under acidic conditions.

The role of pre-treatment is to render the cellulose accessible to enzymes by destructuring the lignocellulosic matrix. Depending on the pre-treatment which is carried out, lignin or hemicelluloses is preferentially attacked, or both at the same time.

Additional steps for adjusting the pH or for liquefaction may be carried out in order to facilitate implementation and the efficiency of the process and in particular the progress of the enzymatic hydrolysis and ethanolic fermentation steps.

The conversion of cellulose into ethanol comprises at least a step for enzymatic hydrolysis of the cellulose into glucose and a step for fermentation of glucose into ethanol, these two steps possibly being carried out separately or simultaneously. When the two steps are operated simultaneously, the process is termed a "SSF process".

The cellulolytic and/or hemicellulolytic enzymes used during the hydrolysis step are produced by a microorganism belonging to the genuses *Trichoderma, Aspergillus, Penicillium* or *Schizophyllum*, or an anaerobic bacterium belonging to the genus *Clostridium*.

The hydrolysis is preferably carried out at a pH in the range 4 to 5.5 and at a temperature in the range 40° C. to 60° C.

The ethanolic fermentation carried out in step d) is accomplished using yeasts or other alcoholigenic microorganisms.

The alcoholigenic microorganisms used during the step for ethanolic fermentation of the hexoses are preferably selected from yeasts and bacteria, possibly genetically modified.

When the alcoholigenic microorganism is a yeast, *Saccharomyces cerevisiae* is that which performs the best. It is also possible to select yeasts such as *Schizosaccharomyces pombe* or *Saccharomyces uvarum* or *diastaticus*. More thermophilic yeasts such as *Kluyveromyces fragilis* (now often known as *K. marxianus*) are also of interest, in particular when enzymatic hydrolysis and ethanolic fermentation are carried out simultaneously (SSF process).

A genetically modified organism such as, for example, a yeast of the *Saccharomyces cerevisiae* type such as TMB 3400 (Ohgren et al, J. of Biotech 126, 488-498, 2006) may also be used. This yeast can be used to ferment a portion of the pentoses into ethanol during the hexose ethanolic fermentation step when glucose is in limiting concentration.

When the alcoholigenic microorganism is a bacterium, *Zymomonas mobilis* is preferred as it has an efficient assimilation pathway.

The ethanolic fermentation of hexoses is preferably carried out at a temperature in the range 30° C. to 40° C., and at a pH in the range 3 to 6.5.

Yeasts, preferably *Saccharomyces cerevisiae*, are the most preferred microorganisms for use. They are the most robust, safe and do not necessitate sterility in order to carry out the process and manage its facilities.

Yeasts of the genus *Saccharomyces* are capable of fermenting hexoses alone (essentially glucose and mannose). These yeasts upgrade the hexoses into ethanol in an optimized manner and can be used to reach conversion yields of the order of 0.46 (w/w) to 0.48 (w/w), which is close to the maximum theoretical yield which is 0.51 (w/w). Only pentoses and a few marginal carbonaceous sources are not used by these yeasts.

When enzymatic hydrolysis and ethanolic fermentation of the hexoses are carried out in one and the same operation (SSF), this operation is preferably carried out at a temperature in the range 30° C. to 45° C., and at a pH in the range 4 to 6.

During step e1), the alcohols and/or solvents produced in step d) or present in step d) following a recycle of ex-pentose ethanolic liquor are purified and separated. They are then separated using any method which is known to the skilled person, in particular by distillation.

During step e2), a solid cake containing the insoluble residue is separated from the stillage containing the sugars which have not been fermented by the alcoholigenic microorganism. The stillage thus contains unfermented pentoses.

Step e2) may be carried out downstream of steps c) and/or d) and may optionally be coupled with washing the cake. Washing may be used to improve recovery of the sugars obtained from hydrolysis (step c), the alcohols and/or solvents produced during step d) or present due to the recycling and/or in addition, sugars which have not been fermented by the microorganism during step d).

During step f) for ethanolic fermentation of pentoses by a microorganism which more specifically ferments pentoses, the sugars contained in the stillage, in particular unfermented pentoses, are also converted into an ex-pentose ethanolic liquor.

The microorganisms used for the fermentation of pentoses may be bacteria, yeasts or fungi.

Bacteria which may be cited include "wild type" bacteria belonging to the genuses *Bacillus, Bacteroides, Thermoanaerobacter* or *Clostridium*, and recombinant bacteria the most interesting of which are *Escherichia coli, Klebsiella oxytoca* and *Zymomonas mobilis*.

Wild type bacteria such as *Pichia stipitis, Candida shehatae* and *Pachysolen Tannophilus*, identified as being the most effective, may be used. Examples of other wild type yeasts mentioned in the literature which may be cited are *Candida guilliermondii* or *Candida tropicalis*.

It is possible to select recombinant yeasts, in particular *Saccharomyces cerevisiae*, such as those described by Olsson and Hahn-Hagerdahl, 1996 or Hahn-Hagerdahl et al. 2007.

A genetically modified organism such as, for example, a yeast of the type *Saccharomyces cerevisiae*, such as TMB 3400 (Ohgren et al, 2006), may also be used for the conversion of pentoses into ethanol, provided that they are supplied with glucose under limiting conditions to allow assimilation of the pentoses.

Fungi are also capable of producing ethanol, including many *Fusarium*, but all of them have poorer performances.

Preferably, yeasts selected from the *Pichia* or *Candida* genuses are used. These microorganisms are more difficult to cultivate than the yeast *Saccharomyces cerevisiae* because they require oxygen in order to produce acceptable performances ("micro-aerobic" conditions, Fromanger et al., J. Ind. Microbiol. Biotechnol, 37, 437-445, 2010) Hahn-Hägerdal et al., 2007). These pentose-fermenting yeasts are also known to be sensitive to inhibiting compounds which alter the performances (Girio et al., Biores Technol, 101, 4775-4800, 2010).

In the process of the present invention, these pentose-fermenting yeasts are advantageously used in a medium which has been partially detoxified by the hexose-fermenting yeast, for example *Saccharomyces cerevisiae*, which is known to reduce the principal aldehydes in particular (Ohgren et al., Applied Biochemistry and Biotechnology vol 121-124, 1055-1067 (2005); Klinke et al., Appl Microbiol Biotechnol 66: 10-26, 2004) such as furfural and 5-HMF.

This is particularly advantageous in the case of the lignocellulosic hydrolysates obtained from pre-treatments carried out under acid conditions such as steam explosion (in the presence of sulphuric acid or $SO_2$) or digestion with dilute acid (sulphuric acid). These pre-treatments generally result in the production of furanic, phenolic and organic acid compounds which are known to be toxic as regards microorganisms.

Preferably, the strain used in the fermentation step f) is a welding of the *Pichia stipitis* or *Candida shehatae* type.

In one embodiment, the pentoses fermented during step f) are contained in the stillage.

Preferably, the stillage, which is sent to the pentose ethanolic fermentation step f) has a sugar concentration in the range 30 to 90 g/L of sugars or fermentiscible products.

If the concentration of sugars or fermentiscible products is not sufficient, in a particular embodiment, that stream can be diverted downstream of the pre-treatment step before sending it to the fermentation step f). This means that the insoluble material is taken up into suspension and causes an enrichment in pentoses and sugars not used in the ethanolic fermentation.

In another embodiment, the pentoses fermented during step f) may be obtained directly at the end of the pre-treatment.

In this variation of the process, a stream containing mainly pentoses is extracted directly during the pre-treatment and is sent to the pentose ethanolic fermentation step. This variation is applicable when the pre-treatment is acidic and comprises a step for the chemical hydrolysis of the hemicelluloses. This is particularly the case when the pre-treatment is steam explosion, carried out under acid conditions. It is then possible to obtain a pentose juice at the outlet from the pre-treatment step, which can be converted into solvents, for example into ABE, or can be used for another application if it is not sent in its entirety to the fermentation step f). This possibility can be used in particular to enhance the dry matter content of the pre-treated plant material which undergoes enzymatic hydrolysis and ethanolic fermentation of the hexoses, or it can even be used to partially detoxify this stream by withdrawing at least a portion of the inhibitors with the pentose juice.

In accordance with yet another embodiment, the pentoses fermented in step f) originate both from the stillage and from a stream withdrawn directly after the pre-treatment step when this is acidic.

Preferably, the concentration of ethanol at the end of the ex-pentose ethanolic fermentation step f) is in the range 5 to 40 g/L, preferably in the range 5 to 30 g/L.

In accordance with the invention, at least a portion of the ex-pentose ethanolic liquor is recycled downstream of pre-treatment step a).

Inactivation of the microorganism which has fermented the pentoses is carried out either by increasing the temperature or by modifying the pH, or by any other technique which is known to the skilled person. pH modification is preferred because it might be necessary to correct the pH for the enzymatic hydrolysis step (step b), after the pre-treatment (step a).

In accordance with one embodiment, the stream containing the ex-pentose ethanolic liquor leaving the pentose ethanolic fermentation step is divided into two streams, one being recycled downstream of the pre-treatment step.

The second stream may be sent to a water/solvent separation step before also being recycled and returned to the reactor where the extraction step e) has taken place.

In accordance with another embodiment, the second stream is used for other applications without recycling.

In accordance with another embodiment, the whole stream containing the ex-pentose ethanolic liquor obtained from fermentation step f) is recycled downstream of the pre-treatment step. In this case, a portion of the stillage obtained from step e) is extracted without being sent to the fermentation step f). The sugars contained in this stillage may be upgraded independently.

The ex-hexose and ex-pentose ethanolic liquors undergoing extraction (step e) may contain 20 to 150 g/L of ethanol. The concentration of ethanol depends on the one hand on the dry matter content, the enzymatic hydrolysis and fermentation steps and on the other hand on any supplements of sugar which might be supplied. It is possible to supplement the medium with sugar, cane sugar or sugar beet or with starchy plants.

The invention will now be described in detail with reference to the figures.

The substrate is introduced into the pre-treatment reactor 2 via the line 1. The reagents and utilities such as the steam necessary to carry out the pre-treatment are introduced via the line 3 and the residues (condensates, black liquor, stillage water, etc.) are withdrawn via the line 4. Recycling, re-use or treatment of this stream is inherent to each type of pre-treatment and is not detailed here.

The pre-treated substrate is withdrawn via the line 6. It preferably contains between 5% (w/v) and 60% (w/v) DM, more preferably between 15% (w/v) and 60% (w/v) DM and still more preferably between 30% (w/v) and 60% (w/v) DM.

Thus, in the embodiment represented in FIG. 1, the pre-treated substrate withdrawn via the line 6 contains the majority of the pentoses in the solid form (pentosanes) or in the soluble form.

In a variation of the process in which the pre-treatment is of the acid type, a stream 5 containing mainly pentoses is withdrawn directly during the pre-treatment and is sent to the reactor 14 in which the pentose ethanolic fermentation takes place.

In accordance with another variation, not shown, a portion of the pentoses may be withdrawn in the stream 5 and a portion in the pre-treated substrate moving in the line 6, and these two streams are mixed in their entirety or in part before the pentose ethanolic fermentation.

Reactor 7 is the reactor in which the conversion of cellulose into ethanol is carried out.

The conditions for enzymatic hydrolysis, principally the dry matter content of the mixture to be hydrolysed and the quantity of enzymes used, are selected such that step c) is carried out in order to be able to dissolve the cellulose in an amount in the range 20% to 99%, in reactor 7, and more particularly between 30% and 95%. The water necessary for obtaining the envisaged DM level is added via the line 8. The desired DM level is in the range 5% (w/v) to 45% (w/v), preferably in the range 8% (w/v) to 35% by weight.

The cellulolytic and/or hemicellulolytic enzymes are added via the line 8a.

The microorganisms used for hexose ethanolic fermentation are introduced via the line 8b.

The additives necessary for adjusting the pH or liquefaction are introduced via the line 8c.

The alcohols and/or solvents produced during the ethanolic fermentation step are extracted in the reactor 11. The alcohol and/or the solvents are preferably extracted by distillation, via the line 12.

The cake containing the insoluble residue is withdrawn via the lines 9a and/or 9b.

In the reactor 11a, the ethanol and/or the solvents are separated and the stillage is withdrawn via the line 13.

More specifically, in the reactor 11b, the ethanol and/or the solvents and water are separated in order to withdraw a stream of products via the line 12.

Thus, at the outlet from steps c) to e) carried out in reactors 7 and 11, the following are obtained: a stream of products 12 (alcohol and/or solvents) withdrawn by any means known to the skilled person, a liquid residue 13 (known as stillage) containing unfermented sugars with in particular pentoses (xylose, arabinose), or even traces of hexoses (galactose, for example, the most difficult hexose to metabolize using conventional yeasts) as well as oligomers and a solid cake containing solid material obtained from the initial substrate (solid residue), and a liquid fraction because of the limitations of the solid/liquid separation equipment. The solid residue is partly composed of cellulose and hemicellulose which has not been hydrolysed, along with lignin.

The microorganism used during the pentose ethanolic fermentation step is introduced into the reactor 14 via the line 15a for mixing with the stillage, fraction 13. The utilities and additives necessary for carrying out the fermentation correctly are introduced via the line 15b. The reactor 14 may be a sterilizable reactor. The fermentation gases are evacuated. The pH in this reactor may be controlled and adjusted as necessary.

The stream leaving the reactor 14 via the line 16 corresponds to the ex-pentose ethanolic liquor. It is not useful to separate the microorganisms.

The aqueous stream entering the reactor for hexose hydrolysis and/or fermentation contains in the range 5 to 40 g/L of ethanol.

In accordance with the embodiment shown in FIG. 1, the stream 16 leaving the pentose ethanolic fermentation step is divided into two streams. The stream 16a is recycled downstream of the pre-treatment step.

The stream 16b may be sent to a water/solvents separation step in a reactor 17, before also being recycled and returned to the separation reactor 11b via a line 18.

In accordance with another embodiment, the stream 16b is used for other applications without recycling.

Figure 2:
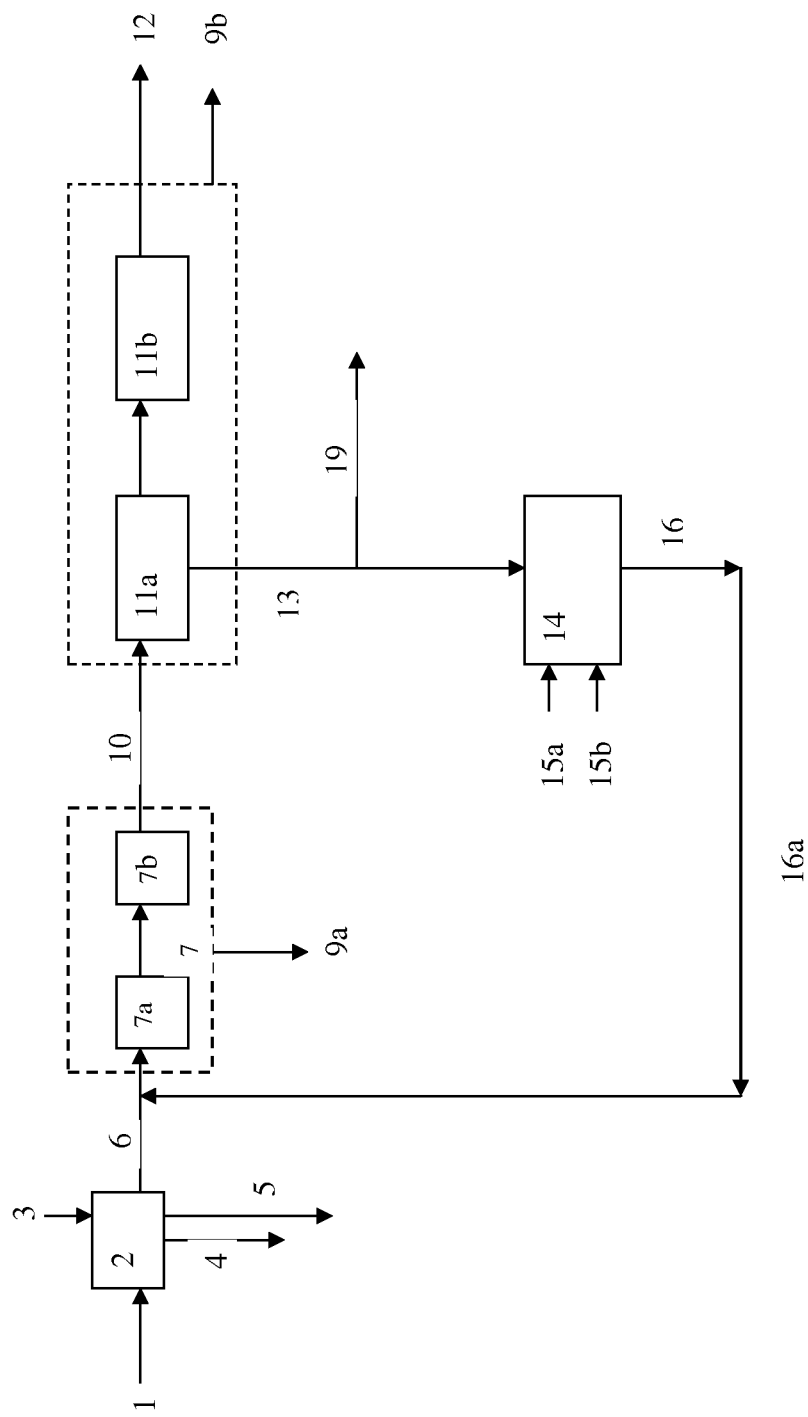
FIG. 2 is a diagrammatic representation of a process for the production of alcohols and/or solvents from lignocellulosic substrates, comprising a step for recycling ex-pentose ethanolic liquor in accordance with a second embodiment.

In the embodiment represented in FIG. 2, all of the stream 16 leaving the pentose ethanolic fermentation reactor is recycled downstream of the pre-treatment step. The excess portion of the stillage which is not sent to the fermentation step f) is withdrawn via the line 19. The sugars contained in this stillage may be independently upgraded.

Because of the process of the invention, the savings made on a single extraction step are substantial. As will be shown in the examples below, it may be up to 40%.

EXAMPLES

The examples below illustrate the invention without in any way limiting its scope.

Example 1 (not in accordance with the invention)

Consider a process for the production of ethanol starting from the fermentation of C6 sugars (hexoses) and C5 sugars (pentoses).

The substrate used was straw, pre-treated under acid conditions. The pre-treated substrate was then neutralized and introduced into the reactor for conversion into ethanol by enzymatic hydrolysis and fermentation of glucose and mannose (sugars containing 6 carbon atoms).

The process treated 52 tones/hour of paste (dry matter base). The composition of the dry material was as follows:

| | |
|---|---|
| Cellulose (%) | 41.7% |
| Xylans (%) | 25.2% |
| Mannans (%) | 0% |
| Lignin (%) | 23.2% |
| Others (%) | 9.9% |

During pre-treatment, the cellulose and hemicellulose losses were of the order of 5% and 10% respectively. At the outlet from the pre-treatment, the dry matter content was 35% (w/v).

The process for the conversion of C6 and C5 sugars into ethanol contained the following steps: enzymatic hydrolysis, ethanolic fermentation of C6 sugars, separation of solid residues from liquor, ethanol distillation, ethanolic fermentation of the stillage cut, and then ethanol distillation. The two ethanol distillation steps could be combined, meaning that only a single ethanol rectification column would be required.

Enzymatic hydrolysis was operated at a pH of 5, with an inlet stream containing 11.8% of dry matter. Under the selected hydrolysis conditions, 95% of sugar polymers were dissolved into monomers.

The sweet juice was then sent for ethanolic fermentation where 90% of the sugars glucose and mannose was converted into ethanol by *Saccharomyces cerevisiae*.

The liquor was sent to a centrifuge in order to separate the solid and liquid phases.

The liquid phase was then sent for distillation. The overhead product contained mainly the ethanol fraction; the bottoms product contained the stillage (mixture of water, pentoses and solids that were still present).

The stillage was sent to the ethanolic fermentation step carried out with a yeast of the species *Pichia stipitis*. The pentoses were respectively converted into ethanol, by-products and microorganisms in an amount of 74.4%, 24.5% and 1.1% by mole respectively.

In the absence of recycling, the ethanol fraction recovered overhead from the distillation was sent to a rectification column to provide an azeotropic ethanol-water mixture.

The products obtained from the pentose ethanolic fermentation were sent to a distillation column to separate out the water then to a rectification column (which could be the same one as that for the ethanol obtained from the hexose fermentation) to produce an azeotropic ethanol-water mixture.

For this process layout, the ethanol production was 14.6 t/h.

The overall energy consumption of the process was 34.6 MW, which corresponded to a mean consumption of 8.55 MJ/kg of solvent produced.

Example 2

The hypothesis of Example 2 was the same as for Example 1, except for recycling the post-pentose fermentation stream to two points of the process.

The first recycle, corresponding to 71% of this stream, was sent upstream of the enzymatic hydrolysis; the remainder was sent to the common station for separating liquor from ethanol. The supplemental water makeup was zero at the enzymatic hydrolysis stage.

The ethanol fraction recovered at the head of the liquor distillation column was sent to a rectification column to separate out the water and the ethanol (an azeotropic ethanol-water mixture).

For this process layout, the ethanol production was 14.46 t/h.

The overall energy consumption of the process was 30.3 MW, which corresponded to a mean consumption of 7.55 MJ/kg of solvent produced.

In accordance with the invention, this example using a layout with two ethanol recycles could be used to obtain an energy saving of 12% compared with Example 1 (MJ/kg of solvent produced).

Example 3

The hypothesis of Example 3 was the same as for Example 1 but differed in a partial recycle of the post-pentose fermentation stream upstream of the enzymatic hydrolysis. The non-recycled portion of the stream was used for other applications.

The recycle, corresponding to 71% of this stream, was sent upstream of the enzymatic hydrolysis. The supplemental water makeup was zero at the enzymatic hydrolysis stage.

The ethanol fraction recovered at the head of the liquor distillation column was sent to a rectification column to separate out the water and the ethanol (an azeotropic ethanol-water mixture).

For this process layout, the ethanol production was 13.11 t/h.

The overall energy consumption of the process was 27.1 MW, which corresponded to a mean consumption of 7.46 MJ/kg of solvent produced.

In this configuration, the amount of equipment required for the process was reduced by one distillation column.

For this example, the layout with a recycle of ethanol obtained from pentose fermentation could be used to obtain an energy saving of 13% compared with Example 1 (MJ/kg of solvent produced).

The invention claimed is:

1. A process for the production of alcohols or solvents or both alcohols and solvents from a cellulosic or lignocellulosic biomass, comprising:
   a) thermochemically pretreating a cellulosic or lignocellulosic substrate to produce a pre-treated substrate;
   b) optionally washing said pre-treated substrate and adjusting the pH of said pre-treated substrate to produce a washed substrate;
   c) enzymatically hydrolyzing said pre-treated substrate and/or optionally washed substrate, with cellulolytic or hemicellulolytic enzymes or both cellulolytic and hemicellulolytic enzymes to produce a hydrolysate and a water-insoluble residue;
   d) fermenting hexoses contained in said hydrolysate of step c) into ethanol and/or solvents by an alcoholigenic microorganism to obtain an ex-hexose ethanolic liquor;
   e) extracting said ethanol or solvent in said ex-hexose ethanolic liquor by:
      e1) separating and purifying said ethanol or solvents or both ethanol and solvents obtained from step d); and
      e2) separating a solid cake containing a water-insoluble residue and obtaining stillage comprising non-fermented pentoses; and
   f) fermenting said pentoses contained in said stillage of step e2 with a pentose-fermenting microorganism and obtaining an ex-pentose ethanolic liquor, wherein at least a portion of said ex-pentose ethanolic liquor obtained in step f) is recycled to step c) or step d), and wherein said microorganisms used in steps d) and f) are different microorganisms.

2. The process of claim 1, wherein said pretreating in step a) is performed under acidic conditions.

3. The process of claim 1, wherein said pentose fermenting microorganism of step f) is *Pichia stipitis* or *Candida shehatae*.

4. The process of claim 1, wherein steps a) and b) are carried out simultaneously at a temperature in the range of 30° C. to 45° C. and at a pH in the range of 4 to 6.

5. The process of claim 1, wherein step e2) is coupled with washing said solid cake.

6. The process of claim 1, wherein said stillage sent to said fermenting of step f) has a sugar concentration in the range of 30 to 90 g/L of sugars.

7. The process of claim 1, wherein all of said stillage obtained in step e2) is sent to step f) and a portion of said ex-pentose ethanolic liquor which is not recycled is sent to a water/solvent separation step before being sent to said extracting of step e).

8. The process of claim 1, wherein only a portion of said stillage is sent to step f).

9. The process of claim 1, wherein at least a portion of said ex-pentose ethanolic liquor obtained in step f) is recycled to step d).

10. The process of claim 1, wherein said cellulolytic and/or hemicellulolytic enzymes of step c) are produced by a microorganism of the genus *Trichoderma, Aspergillus, Penicillium*, or *Schizophyllum*, or an anaerobic bacterium of the genus *Clostridium*.

11. The process of claim 1, said alcoholigenic microorganism of step d) is a yeast.

12. The process of claim 11, wherein said yeast is *Schizosaccharomyces pombe, Saccharomyces uvarum* or *diastaticus*, or *Kluyveromyces fragilis*.

* * * * *